March 12, 1974 H. HOLTKAMP Plant Pat. 3,515
AFRICAN VIOLET
Filed Aug. 24, 1972
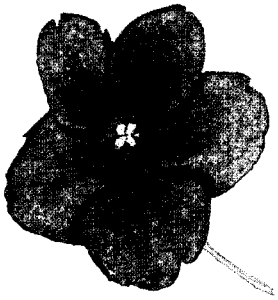
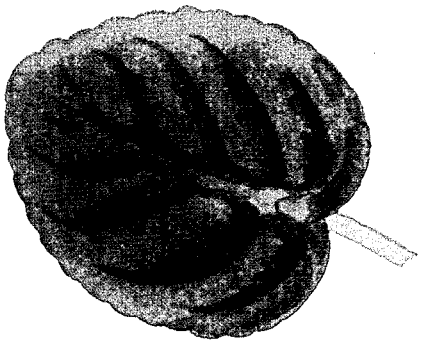
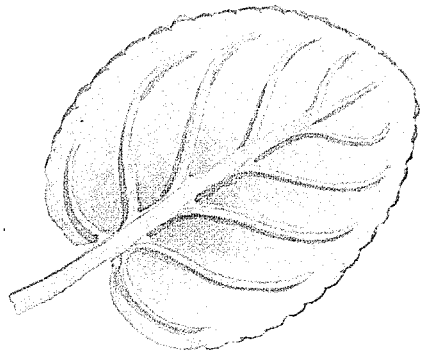
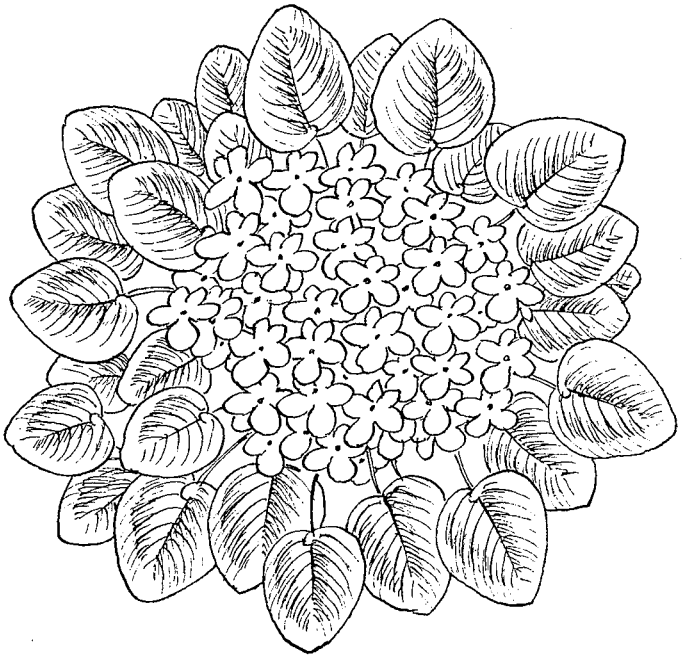

United States Patent Office

Plant Pat. 3,515
Patented Mar. 12, 1974

3,515
AFRICAN VIOLET

Hermann Holtkamp, Werther Strasse 5–7, Postfach 19, 4243 Isselburg, Germany

Filed Aug. 24, 1972, Ser. No. 283,586
Int. Cl. A01h 5/00
U.S. Cl. Plt.—69 1 Claim

ABSTRACT OF THE DISCLOSURE

A hybrid violet of a descendant of a cross between *Saintpaulia ionantha* and *Saintpaulia shumensis* species which has permanent characteristics including strength of stem, fast and vigorous growth, profuse flowering, uniform bouquet, prolonged blooming period, resistance to disease, reliability in initiating new plantlets, retention of flowers past maturity on their respective stems, and uniformity throughout the life cycle.

BRIEF SUMMARY

A sport of the "Rhapsodie" Elfriede variety disclosed in my United States Letters Patent No. PP 3,147 of May 2, 1972, having substantially the same characteristics as the parent plant as described in said patent, except for the color of the flowers, which is red-violet.

Asexual reproduction of my new variety by leaf cuttings, as performed by me at Isselburg, Rhineland, Germany, shows that the foregoing characteristics and distinctions come true to form and are established and transmitted through succeeding propagations.

DESCRIPTION OF DRAWINGS

The upper illustrations show, in full color, one of the flowers, and the opposite sides of one of the leaves; and below, in pen and ink, a top plan view in reduced size of a plant showing a flower head and a wreath of leaves therearound.

DETAILED DESCRIPTION

The present variety is a sport of "Rhapsodie" Elfriede Type 10/183 which is fully described in the above Letters Patent.

Name: "Rhapsodie" Veronika
Parent: "Rhapsodie" Elfriede Type 10/183
Leaves: Borne in rosette arrangement around a central flower head Flowers: Borne profusely in a large central flower head which is approximately from 5½ to 6½ inches in diameter
Individual flowers: Quinquepartite, bilaterally symmetrical
*Size.*—1¼ to 3¾ inches in diameter
*Color.*—Red-violet
*Calyx.*—Quinquepartite
*Peduncles.*—Multiflorous, up to 4 inches long, borne in compact cynes with 8–20 flowers at second blooming The following color designations are according to "Dictionary of Color" by Maerz and Paul:

| | Plate Letter | No. |
|---|---|---|
| Main body of flower: | | |
| Red-violet | 43 K | 9 |
| Anthers—golden yellow | 9 L | 1 |

GENERAL CHARACTERISTICS

While there may be minor variations in the leaf size, shape and color, and in the shape of the flowers, which are common to African violets, there is substantial uniformity in all the other characteristics described in the aforesaid patent.

Thus in the present variety, the characteristics that are constant and that distinguish it from the other varieties include: (a) the large central flower head of from approximately five and one-half to six and one-half inches in diameter at second blooming, the flowers of which are of a red-violet color, and (b) the wreath or collar of dark green leaves surrounding the flower head of the color described.

The flower head itself contains from six to eight stems at first blooming with approximately six blooms on each stem at first blooming and approximately double that number at second blooming.

I claim:

1. A distinct variety of African violet substantially as herein shown and described, characterized by a habit of bearing a large, central flower head of approximately five and one-half to six and one-half inches in diameter at second blooming supporting the flowers of each flower head above a wreath of dark green leaves, which flowers have petals of a distinctive and attractive red-violet color.

No references cited.

ROBERT E. BAGWILL, Primary Examiner